United States Patent [19]

Jaeger et al.

[11] 4,223,166
[45] Sep. 16, 1980

[54] PROCESS FOR PRODUCING 4-BROMO-2-CHLOROPHENOLS

[75] Inventors: Roland Jaeger, Mulhouse, France; Kurt Huber, Möhlin, Switzerland

[73] Assignees: Societe Anonyme pour l'Industrie Chimique, Mulhouse, France; Ciba-Geigy Corporation, Ardsley, N.Y.

[21] Appl. No.: 14,515

[22] Filed: Feb. 23, 1979

Related U.S. Application Data

[63] Continuation-in-part of Ser. No. 935,281, Aug. 21, 1978, abandoned.

[30] Foreign Application Priority Data

Aug. 26, 1977 [CH] Switzerland .......................... 010454

[51] Int. Cl.$^2$ .......................................... C07C 39/24
[52] U.S. Cl. .................................................. 568/779
[58] Field of Search ............................. 568/779, 776

[56] References Cited

U.S. PATENT DOCUMENTS

| | | | |
|---|---|---|---|
| 2,452,154 | 10/1948 | Ross | 568/779 |
| 3,449,443 | 6/1969 | Dietzler et al. | 568/779 |
| 3,471,578 | 10/1969 | Odenweller | 568/779 |

FOREIGN PATENT DOCUMENTS

2144259 3/1972 Fed. Rep. of Germany ........... 568/776

OTHER PUBLICATIONS

Kosower et al., p. 7 P, Abstract of papers 138th Meeting Americ. Chem. Soc. Sep. 11–16, 1960.

*Primary Examiner*—Werren B. Lone
*Attorney, Agent, or Firm*—Harry Falber

[57] ABSTRACT

A process for the production of 4-bromo-2-chlorophenols of the formula

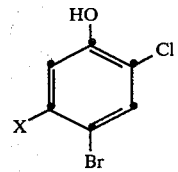

wherein X represents hydrogen or chlorine is disclosed which process comprises the bromination of a 2-chlorphenol of the formula

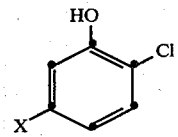

wherein X has the meaning given above in the presence of a compound of the formula

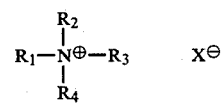

in which
  $R_1$ represents an alkyl group having 1 to 8 carbon atoms, or the phenyl or benzyl group,
  $R_2$ and $R_3$ independently of one another represent an alkyl group having 1 to 8 carbon atoms,
  $R_4$ represents hydrogen, or an alkyl group having 1 to 8 carbon atoms, and
  X represents chlorine, bromine, or iodine or the hydrogen sulfate anion.

The new process substantially avoids the undesired formation of the 2,6-isomers and the 4-bromo-2-chlorophenols are obtained in excellent purity.

9 Claims, No Drawings

PROCESS FOR PRODUCING 4-BROMO-2-CHLOROPHENOLS

This is a continuation-in-part application of application Ser. No. 935,281, filed Aug. 21, 1978, now abandoned.

The present invention relates to a process for producing 4-bromo-2-chlorophenols of formula I

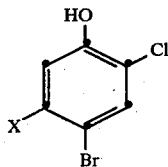

wherein X represents hydrogen or chlorine by bromination of a 2-chlorophenol of formula II

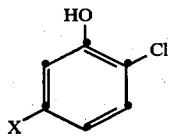

wherein X has the meaning given above.

The 4-Bromo-2-chlorophenols of formula I are valuable intermediates for producing insecticidal and acaricidal active substances. To be mentioned among these are in particular the O-ethyl-S-n-propyl-O-(4-bromo-2-chlorophenyl)-thiophosphoric acid ester, the production and use of which are described in the U.S. Pat. No. 3,839,511, and the O,O-dimethyl-O-(4-bromo-2,5-dichlorophenyl)-thiophosphoric acid ester, the production and use of which are described in U.S. Pat. No. 3,227,610.

It is known that 4-bromo-2-chlorophenol can be produced by reacting 2-chlorophenol with bromine at room temperature in carbon tetrachloride. The desired 4-bromo-2-chlorophenol is obtained in this manner in a yield of 87% of theory (see Ch. Raiford et al., J. Amer. Chem. 55, 2125–2131 (1933)).

Furthermore, it is known from the U.S. Pat. No. 3,449,443 that on reaction of 2-chlorophenol with bromine chloride in carbon tetrachloride at 0° C. there is formed, besides 74% of theory of 2-bromo-6-chlorophenol, only 22% of theory 4-bromo-2-chlorophenol; and at 23° to 26° C. there is formed, besides 61.7% of theory of 2-bromo-6-chlorophenol, only 26.3% of theory of 4-bromo-2-chlorophenol.

From the German Offenlegungsschrift No. 2,144,259 is also known the procedure of reacting phenols in the melt, in the presence of brominating catalysts such as iron, aluminium, iron halides, aluminium halides and iodine or mixtures of these substances, with a mixture of bromine and chlorine. This process yields however exclusively highly brominated compounds.

The processes mentioned above are lacking above all in that they are insufficiently selective with regard to the formation of the desired 4-bromo-2-chlorophenol. This leads on the one hand to losses in yield, and on the other hand to the necessity of separating the isomers which are always concomitantly formed, especially the 2,6-isomer, since these impair the effectiveness of the final products; and this separating operation constitutes and undesirable additional expenditure.

It is therefore the object of the present invention to provide a process by which 2-chlorophenols can be brominated in the 4-position more selectively than it can be by the processes known hitherto.

It has been found that the 4-bromo-2-chlorophenols of formula I can be produced with excellent selectivity by brominating a 2-chlorophenol of formula II in the presence of a compound of the formula III

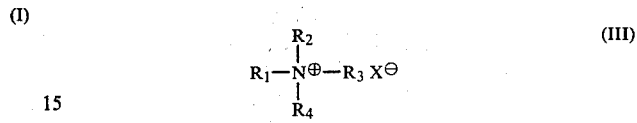

in which

R$_1$ represents an alkyl group having 1 to 8 carbon atoms, or the phenyl or benzyl group, R$_2$ and R$_3$ independently of one another respresent an alkyl group having 1 to 8 carbon atoms, R$_4$ represents hydrogen, or an alkyl group having 1 to 4 carbon atoms, and X represents chlorine, bromine, iodine or the hydrogen sulfate anion.

The bromination of 2-chlorophenols of the formula II by the process according to the invention can be performed either in the presence or in the absence of an inert solvent. Suitable solvents are for example halogenated hydrocarbons, such as methylene chloride, chloroform, carbon tetrachloride, 1,2-dichloroethane, 1,1-dichloroethane, 1,1,1-trichloroethane, chlorobenzene, o-dichlorobenzene or Frigen-113 (trichlorotrifluoroethane). Furthermore, hydrocarbons such as hexane, benzene, toluene and xylenes are likewise suitable. With the absence of a solvent, the process according to the invention is performed in the melt.

The process according to the invention is performed at temperatures within the range of 0° to 60° C. In the case where the reaction is performed in a solvent, the preferred temperature range is between 0° and 20° C.; and in the melt the reaction is performed in each case preferably just above the melting point of the reaction mixture. This means in practice that the bromination in the melt is commenced at low temperature, and the temperature is successively raised in the course of bromination. When 4-bromo-2-chlorophenol is produced by melt bromination, the reaction is performed for example initially at 0° C., and the temperature during the course of bromination is gradually raised, to an extent corresponding to the rising melting point of the reaction mixture.

The compounds of the formula III are added according to the invention in amounts of 1 to 10 percent by weight, preferably 3 to 6 percent by weight, relative to the employed amount of 2-chlorophenol.

Suitable compounds of the formula III are hydrochlorides, hydrobromides, hydroiodides and hydrogen sulfates of tertiary amines, such as trimethylamine hydrochloride, trimethylamine hydrobromide, triethylamine hydrochloride, triethylamine hydrobromide, triethylamine hydroiodide, tributylamine hydrochloride, tributylamine hydrobromide, tributylamine hydrogen sulfate or trioctylamine hydrochloride, and also quaternary ammonium salts, such as trimethylethylammonium bromide, trimethylethylammonium chloride, trimethylethylammonium iodide, trimethylphenylammonium chloride, triethylphenylammonium chloride, trimethylbenzylammonium chloride, trimethylbenzylammonium bromide and trimethylbenzylammonium hydrogen sulfate.

As brominating agents it is possible to use according to the invention elementary bromine, mixtures of chlorine and bromine, bromine chloride, N-bromine compounds such as N-bromosuccinimide, or hypobromites. Elementary bromine is preferred amongst these brominating agents. The brominating agent is used in stoichiometric amounts, or in a slight excess of up to 0.02 mole of bromine per mole of 2-chlorophenol of formula II. It is also possible however to use the brominating agent in an amount slightly less than the equivalent amount, and after bromination to remove the unreacted 2-chlorophenol by distillation.

It is possible by the process according to the invention to convert 2-chlorophenols of formula II, with excellent selectivity, into 4-bromo-2-chlorophenols of formula I. The 2-chlorophenols of formula II are converted practically quantitatively into bromochlorophenols of formula I. The resulting reaction products contain when the process according to the invention is performed in an inert solvent about 1 percent by weight of undesired 2,6-isomer, and when performed in the melt about 2 percent of undesired 2,6-isomer. The 4-bromo-2-chlorophenols of formula I produced according to the invention are therefore suitable, without further purification, as intermediates for producing insecticidal phosphoric acid esters, particularly O-ethyl-S-n-propyl-O-(2-chloro-4-bromophenyl)-thiophosphate and O,O-dimethyl-O-(4-bromo-2,5-dichlorphenyl)-thiophosphate. Compared with the processes known hitherto, the process according to the invention has the advantage that on the one hand the yield of 4-bromo-2-chlorophenol is increased, and on the other hand that expensive purifying operations on the intermediates produced are rendered unnecessary.

The process according to the invention is further illustrated by the following Examples.

EXAMPLE 1

To a solution of 257.0 g (2 moles) of 2-chlorophenol in 350 g of 1,1,1-trichloroethane is added, after the addition of a compound of the formula I, in the course of 2 hours at 5° to 18° C. a total amount of 320 g (2 moles) of bromine. The addition of the bromine is made at the following temperatures:

| | |
|---|---|
| 5° to 12° C. | 230 g of bromine |
| 12° to 15° C. | 60 g of bromine |
| 15° to 18° C. | 30 g of bromine |
| total: | 320 g of bromine |

The hydrogen bromide escaping from the reaction mixture is absorbed in aqueous sodium hydroxide solution. After the bromine has been added, the reaction mixture is refluxed for a short time. The solvent is subsequently removed in vacuo. The yield of bromophenol is practically quantitative (>98% of theory). Further experimental data with regard to type and amount of compound of the formula I added and the amount of 2,6-isomers contained in the reaction mixture are given in the Table which follows.

| Compound of the formula I | Amount (g) | Percent by weight of 2,6-isomer in the final product |
|---|---|---|
| — | — | 2.3–2.5 |
| $N(CH_3)_3 \cdot HCl$ | 12 | 0.9 |
| $N(C_2H_5)_3 \cdot HCl$ | 12 | 0.9 |
| $N(C_2H_5)_3 \cdot HCl$ | 6 | 1.5 |
| $N(C_2H_5)_3 \cdot HCl$ | 18 | 0.9 |
| $N(C_8H_{17})_3 \cdot HCl$ | 12 | 1.5 |
| $\oplus N(CH_3)_3 C_2H_5 \, Br^\ominus$ | 12 | 0.9 |
| $\oplus N(CH_3)_3 C_2H_5 \, Cl^\ominus$ | 12 | 0.9 |
| $\oplus N(CH_3)_3 C_2H_5 \, Cl^\ominus$ | 30 | 0.9 |
| $\oplus N(CH_3)_3 CH_2-C_6H_5 \, Cl^\ominus$ | 12 | 0.9 |
| $n(C_2H_5)_3 \cdot HBr$ | 22 | 0.6 |

EXAMPLE 2

257.0 g (2 moles) of 2-chlorophenol is dissolved in 350 g of chlorobenzene and, after the addition of 12 g of triethylamine hydrochloride, the mixture is brominated by the method described in Example 1. The yield obtained is 411.2 g (99.1% of theory) of 4-bromo-2-chlorophenol, which contains merely 0.6 percent by weight of 6-bromo-2-chlorophenol.

EXAMPLE 3

81.5 g (0.5 mole) of 2,5-dichlorophenol is dissolved in 120 g of chlorobenzene. After addition of 4.1 g (0.03 mole) of triethylamine hydrochloride the mixture is cooled to 5° C. Then 80.0 g (0.5 mole) of bromine is added during 3 hours. During the first hour of bromine addition the temperature of the reaction mixture is kept at 5° to 8° C. At the end of the bromine addition the temperature is allowed to raise to about 15° C. During the addition of bromine an evolution of hydrogen bromide gas can be observed. After the addition of bromine the reaction mixture is stirred at 15° to 20° C. for 1 hour. Then the solvent is distilled off in vacuo at 70° C./15 to 20 torr.

126.0 g of product is obtained containing 94% by weight of 4-bromo-2,5-dichlorophenol (118.4 g) which corresponds to a yield of 98% of the theoretical amount calculated on 2,5-dichlorophenol. The product contains 0.5 to 1% by weight of 6-bromo-2,5-dichlorophenol.

The same result is obtained when the triethylamine hydrochloride is replaced with 5.0 g (0.03 mole) of ethyl-trimethyl ammonium bromide.

When the bromination of 2,5-dichlorophenol is carried out under the same conditions but in the absence of a compound of formula III, such as triethylamine hydrochloride and ethyl-trimethylammonium bromide, there are obtained 124.0 g of product containing 88% by weight (109.1 g) of 4-bromo-2,5-dichlorophenol which corresponds to a yield of 90% of the theoretical amount calculated on 2,5-dichlorophenol. The product contains 5 to 6% by weight of 6-bromo-2,5-dichlorophenol as by-product.

What is claimed is:

1. A process for producing 4-bromo-2-chlorophenols of formula I

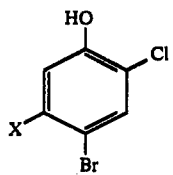

wherein X represents hydrogen or chlorine by bromination of a 2-chlorophenol of formula II

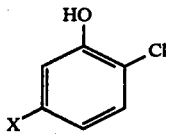

wherein X has the meaning given above, which process comprises brominating a 2-chlorophenol of formula II at a temperature of from about 0°–60° C. and with from about stoichiometric amounts up to an excess of 0.02 mole of bromine per mole of said 2-chlorophenol in the presence of from about 1–10%, by weight of said 2-chlorophenol, of a compound of the formula III

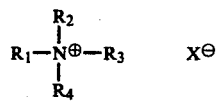

in which

R₁ represents an alkyl group having 1 to 8 carbon atoms, or the phenyl or benzyl group, R₂ and R₃ independently of one another represent an alkyl group having 1 to 8 carbon atoms, R₄ represents hydrogen, or an alkyl group having 1 to 8 carbon atoms, and X represents chlorine, bromine, iodine, or the hydrogen sulfate anion.

2. A process according to claim 1, wherein the bromination of a 2-chlorophenol of formula II is performed in the presence of an inert solvent.

3. A process according to claim 1, wherein the bromination of a 2-chlorophenol of formula II is performed in the presence of methylene chloride, chloroform, carbon tetrachloride, 1,2-dichloroethane, 1,1-dichloroethane, 1,1,1-trichloroethane, chlorobenzene or o-dichlorobenzene, as solvent.

4. A process according to claim 1, wherein the bromination of a 2-chlorophenol of formula II is performed in the melt, in the absence of a solvent.

5. A process according to claim 1, wherein the bromination of a 2-chlorophenol of formula II is performed in the presence of an inert solvent in the temperature range of between 0° and 20° C.

6. A process according to claim 1, wherein the bromination of a 2-chlorophenol of formula II is performed in the melt in each case just above the melting point of the reaction mixture.

7. A process according to claim 1, wherein there is used 3 to 6 percent by weight of a compound of the formula III, relative to the employed 2-chlorophenol of formula II.

8. A process according to claim 1, wherein there are used as brominating agents: elementary bromine, mixtures of chlorine and bromine, bromide chloride, N-bromosuccinimide or hypobromites.

9. A process according to claim 1, wherein the brominating agent used is elementary bromine.

* * * * *